United States Patent [19]
Van der Aa et al.

[11]   4,216,217
[45]   Aug. 5, 1980

[54] NOVEL (1-ARYLCYCLOALKYLMETHYL) ISOTHIOCYANATES

[75] Inventors: Marcel Van der Aa, Vosselaar; Raymond Stokbroekx, Beerse, both of Belgium

[73] Assignee: Janssen Pharmaceutica N.V., Beerse, Belgium

[21] Appl. No.: 39,613

[22] Filed: May 16, 1979

Related U.S. Application Data

[63] Continuation-in-part of Ser. No. 950,968, Oct. 13, 1978, abandoned.

[51] Int. Cl.$^2$ .......................... A01N 9/00; A01N 9/18; C07C 161/02; C07D 333/00

[52] U.S. Cl. ..................................... 424/263; 424/275; 424/302; 546/331; 549/75; 260/454

[58] Field of Search ................. 260/454, 329 S, 332.5, 260/332.3 R, 429 R, 429.9, 439 R, 438.1; 546/331; 424/302, 275, 263, 287, 245; 549/75

[56]   References Cited
U.S. PATENT DOCUMENTS 3,367,957   2/1968   Newallis et al. ..................... 260/454

Primary Examiner—Alan Siegel
Attorney, Agent, or Firm—Geoffrey G. Dellenbaugh

[57]   ABSTRACT

This invention relates to novel (1-arylcycloalkylmethyl) isothiocyanates, having biocidal, more particularly, fungicidal, bactericidal and insecticidal properties.

4 Claims, No Drawings

NOVEL (1-ARYLCYCLOALKYLMETHYL) ISOTHIOCYANATES

CROSS-REFERENCES TO RELATED APPLICATIONS

This is a continuation-in-part of our copending application Ser. No. 950,968, filed Oct. 13, 1978 now abandoned.

BACKGROUND OF THE INVENTION

In Brit. Pat. No. 892,790 and in U.S. Pat. No. 3,367,957 there are described respectively the compounds methyl isothiocyanate and cyclopropylmethyl isothiocyanate both as nematocides.

The present invention relates to a novel class of biocidal (1-arylcycloalkylmethyl)isothiocyanates which differ from the aforementioned cyclopropylmethyl isothiocyanate by the presence of an aryl radical in the 1-position of the cycloalkane ring.

DESCRIPTION OF THE PREFERRED EMBODIMENTS:

This invention is concerned with novel (1-arylcycloalkylmethyl)isothiocyanates which may structurally be represented by the formula (I)

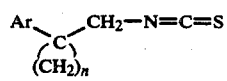

wherein
Ar is a member selected from the group consisting of thienyl, halothienyl, naphthalenyl, pyridinyl, phenyl and substituted phenyl, said substituted phenyl having from 1 to 3 substituents, each independently selected from the group consisting of lower alkyl, lower alkyloxy, lower alkylthio, halo, amino, nitro, cyano and trifluoromethyl; and
n is an integer of from 2 to 5 inclusive.

In the foregoing and in the following definitions, the term "halo" is generic to fluoro, chloro, bromo and iodo; the term "lower alkyl" is meant to include straight and branched hydrocarbon radicals, having from 1 to 6 carbon atoms, such as, for example, methyl, ethyl, propyl, butyl, pentyl, hexyl, 1-methylethyl, 1,1-dimethylethyl and the like.

The compounds of formula (I) may be prepared by the application of methodologies known in the art, as described, for example, in Saul Patai Ed. "The chemistry of cyanates and their thioderivatives" John Wiley & Sons Chichester-New York-Brisbane-Toronto (1977) p. 1013–1053. One method of preparing the compounds (I) is by the reaction of the amine (II) with carbon disulfide (III) to obtain a dithiocarbamate of formula (IV) and subsequently converting the latter into the desired isothiocyanate (I) by the reaction of (IV) with an appropriate decomposing agent, e.g. a lower alkyl chloroformate (V), preferably ethyl chloroformate. The foregoing reactions are illustrated as follows:

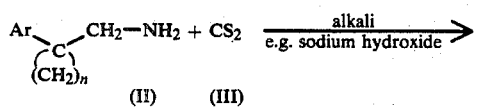

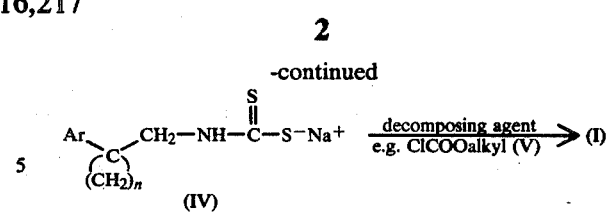

Said reaction of the amine (II) with carbon disulfide (III) is conveniently carried out in an appropriate reaction-inert solvent such as, for example, water; a lower alcohol, e.g. methanol; an alifatic-, alicyclic- or aromatic hydrocarbon, e.g. hexane, cyclohexane or benzene; a halogenated hydrocarbon, e.g. trichloromethane; an alifatic- or alicyclic ether, e.g. 1,1'-oxybispropane or 1,4-dioxane; and the like. The reaction is preferably carried out in the presence of an appropriate base such as, for example, an alkaline- or an earth alkaline metal hydroxide, e.g. sodium hydroxide; a tertiary amine, e.g. N,N-diethylethanamine and the like. Preferably the reaction-temperature is kept below room temperature and, most preferably, between 0° C. and 10° C.

The decomposition-reaction of the dithiocarbamate (IV) by its reaction with the lower alkyl chloroformate (V) is suitably conducted in an appropriate reaction-inert solvent, e.g. one of the solvents described hereabove for the reaction of (II) with (III). Bases such as alkaline metal- or earth alkaline metal hydroxide, e.g. potassium hydroxide, or tertiary amines, e.g. N,N-diethylethanamine are taught to have a catalytic effect on the decomposition of the intermediately formed carbalkoxydithiocarbamate (VI) (See, e.g. J. Am. Chem. Soc. 83, 2532–2536 (1961)). Somewhat elevated temperatures may be used to enhance the reaction-rate.

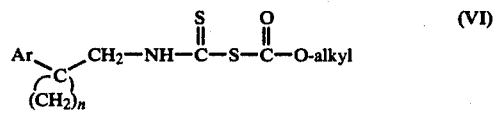

The amines of formula (II), used as staring materials herein, are generally known and they may all be prepared following methods described in the literature for the preparation of such known or similar compounds.

The isothiocyanates of formula (I) possess valuable biocidal properties and as such they can be used in a wide variety of circumstances.

More particularly, the subject compounds have fungicidal, bactericidal and insecticidal properties, and as a result they can be used to combat any unwanted growth of fungi or bacteria or to kill insects.

The compounds of formula (I) are especially useful as preservatives of organic materials which are susceptible to attack by noxious microorganisms and insects. They can be used, for example, for the preservation of technical and agricultural products, such as, for example, wood, fibers, textiles, jute, cork, paper, dyes, etc., and as desinfectants in veterinary medium and human hygiene. The subject compounds are also active against marine organisms and as such they can be used as antifouling agents.

The useful biocidal properties of the compounds of formula (I) are clearly illustrated in the following experiments.

A. INSECTICIDAL ACTIVITY AGAINST THE HOUSE-FLY (MUSCA DOMESTICA)

Test solutions are prepared by dissolving the test-compounds in 2-propanone at a concentration of 2.5% and further diluting the thus obtained stock-solution with water to obtain final concentrations of the active ingredient of respectively 0.02, 0.01, 0.005 and 0.0025%.

1 ml of the test solution is poured onto a filter paper of 11 cm diameter. The filter paper is covered by a petri-dish of 11 cm diameter and 10 flies are confined in the space between the filter paper and the petri-dish.

Insecticidal activity of the test compound is assessed 1, 4 and 24 hours thereafter by counting the number of flies that are respectively alive, knocked-down or dead.

The useful insecticidal properties of the compounds of formula (I) are clearly illustrated by the results presented in the following table I.

Table I

| | | Efficacy of compounds (I) against house-fly | | | | | | | |
|---|---|---|---|---|---|---|---|---|---|
| | | | \multicolumn{9}{c}{Number of flies alive (L), knocked-down (KD) and dead (D)} |
| | | | After 1 hour | | | After 4 hours | | | After 24 hours | | |
| Compound | Conc. of act. ingredient in test solution | L | KD | D | L | KD | D | L | KD | D |
|  | 0.02% | 8 | 2 | 0 | 0 | 2 | 8 | 0 | 0 | 10 |
| | 0.01% | 9 | 1 | 0 | 3 | 3 | 4 | 0 | 0 | 10 |
| | 0.005% | 8 | 2 | 0 | 6 | 3 | 1 | 0 | 0 | 10 |
| | 0.0025% | 10 | 0 | 0 | 8 | 1 | 1 | 2 | 2 | 6 |
| 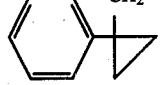 | 0.02% | 8 | 2 | 0 | 4 | 0 | 6 | 0 | 0 | 10 |
| | 0.01% | 8 | 2 | 0 | 3 | 3 | 4 | 0 | 0 | 10 |
| | 0.005% | 9 | 1 | 0 | 3 | 5 | 2 | 0 | 0 | 10 |
| | 0.0025% | 10 | 0 | 0 | 10 | 0 | 0 | 4 | 1 | 5 |

B. ACTIVITY AGAINST WOOD-ATTACKING FUNGI

The tests are performed in petri-dishes of 50 mm diameter using a solid malt-agar medium. The test compound is incorporated into the medium by mixing the latter, before solidification, with a solution of the test compound in 50% ethanol to obtain concentrations of the active ingredient of from 0.1 to 100 ppm (parts per million). After solidification of the medium inoculation is performed by applying a piece of mycelium to the center of each petri-dish. Antifungal activity is evaluated 7 and 14 days after inoculation by estimating the surface of each petri-dish which is covered by mycelium of the fungus. The results, represented in the following table II, are expressed according to the following score system:

score 0 = no growth
score 1 = ≦25% growth as compared to untreated control.
score 2 = 25 to 50% growth as compared to untreated control.
score 3 = 50 to 75% growth as compared to untreated control.
score 4 = >75% growth as compared to untreated control.

For each test 2 scores are given, representing respectively the evaluations made after 7 and 14 days.

Table II

| | | Activity of compounds (I) against wood-attacking fungi | | | | | | | |
|---|---|---|---|---|---|---|---|---|
| | | \multicolumn{8}{c}{Antifungal scores} |
| | Concentration of act. ingredient in ppm | Coniophora cerebella | | Coriolus versicolor | | Poria monticola | | Pullularia pullulans | |
| Compound | | 7 d. | 14d. | 7 d. | 14d. | 7 d. | 14d. | 7 d. | 14d. |
| 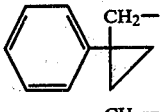 | 100 | 0 | 0 | 0 | 0 | 0 | 0 | 1 | 3 |
| | 10 | 0 | 0 | 4 | 4 | 0 | 0 | 4 | 4 |
| | 1 | 3 | 4 | 4 | 4 | 4 | 4 | 4 | 4 |
| | 0.1 | 4 | 4 | 4 | 4 | 4 | 4 | 4 | 4 |
|  | 100 | 0 | 0 | 0 | 0 | 0 | 0 | 2 | 4 |
| | 10 | 0 | 0 | 0 | 0 | 0 | 0 | 4 | 4 |
| | 1 | 3 | 4 | 4 | 4 | 4 | 4 | 4 | 4 |
| | 0.1 | — | — | — | — | — | — | — | — |

In view of the aforementioned biocidal activities of the compounds of the invention this invention further provides valuable compositions comprising at least one of the isothiocyanates of formula (I) as an active ingredient, if desired, in admixture with other biocidal active agents, in a solvent or a solid, a semi-solid or a liquid diluent or a carrier.

The active agents can be used in suitable solvents or diluents in the form of emulsions, suspensions, dispersions or ointments, on suitable solid or semi-solid carrier substances, in ordinary or synthetic soaps, detergents or dispersion media.

Solid carrier substances which are suitable for the preparation of compositions in powder form include various inert, porous and pulverous distributing agents of inorganic or organic nature such as, for example, tricalcium phosphate or calcium carbonate, in the form of prepared chalk or ground limestone, kaolin, bole, bentonite, talcum, silicic acid or boric acid; powdered cork, sawdust, and other fine pulverous materials of vegetable origin are also carrier substances.

The isothiocyanates are mixed with these carrier substances, for example, by being ground therewith; alternatively, the inert carrier substance is impregnated with a solution of the active component in a readily volatile solvent and the solvent is thereafter eliminated by heating or by filtering with suction at reduced pressure. By adding wetting and/or dispersing agents, pulverous preparations can also be made readily wettable with water, so that suspensions are obtained.

Inert solvents used for the production of liquid preparations should preferably not be readily inflammable and as far as possible non-toxic to warm-blooded animals or plants in the relevant surroundings. Solvents suitable for this purpose are high-boiling oils, for example, of vegetable origin, and lower-boiling solvents, such as, for example, isopropanol, dimethylsulfoxide, hydrogenated naphthalenes and alkylated naphthalenes. It is of course, also possible to use mixtures of solvents. Solutions can be prepared in the usual way, if necessary, with assistance of solution promoters. Other liquid forms which can be used consist of emulsions or suspensions of the active compound in water or suitable inert solvents, or also concentrates for preparing such emulsions, which can be directly adjusted to the required concentration. For this purpose, the isothiocyanates are, for example, mixed with a dispersing or emulsifying agent. The active component can also be dissolved or dispersed in a suitable inert solvent and mixed simultaneously or subsequently with a dispersing or emulsifying agent.

It is also possible to use semi-solid carrier substances of a cream ointment, paste or waxlike nature, into which the isothiocyanates can be incorporated, if necessary, with the aid of solution promoters and/or emulsifiers. Vaseline and other cream bases are examples of semi-solid carrier substances.

Furthermore, it is possible for the isothiocyanates to be used in the form of aerosols. For this purpose, the active component is dissolved or dispersed, if necessary, with the aid of suitable inert solvents as carrier liquids, such as difluorodichloromethane, which at atmospheric pressure boils at a temperature lower than room temperature, or in other volatile solvents. In this way, solutions under pressure are obtained which, when sprayed, yield aerosols which are particularly suitable for controlling or combating fungi and bacteria, e.g. in closed chambers and storage rooms, and for application to vegetation for eradicating or for preventing infection by fungi or bacteria.

The isothiocyanates and the compositions thereof can be applied by conventional methods. For example, a growth of microorganisms or a material to be treated or to be protected against attack by microorganisms can be treated with the isothiocyanates and the compositions thereof by dusting, sprinkling, spraying, brushing, dipping, smearing, impregnating or other suitable means.

When the isothiocyanates are employed in combination with suitable carriers, e.g., in solution, suspension, dust, powder, ointment, emulsion and the like forms, a high activity over a very high range of dilution is observed. For example, concentrations of the active ingredient ranging from 0.1 to 10 percent by weight, based on the weight of composition employed, have been found effective in combating microorganisms.

Higher concentrations may naturally also be employed as warranted by the particular situation.

The compounds of formula (I) may be applied alone or optionally together with other biocidal substances, e.g., bactericides, fungicides, insecticides etc.. When used in the preservation of organic material, particularly wood, it has been found advantageous to combine the isothiocyanates of formula (I) with antimicrobial imidazole and triazole derivatives such as for example, 1-[2-(2,4-dichlorophenyl)-2-(2-propenyloxy)ethyl]-1H-imidazole, 1-[2-(2,4-dichlorophenyl)-1,3-dioxolan-2-ylmethyl]-1H-1,2,4-triazole, 1-[2-(2,4-dichlorophenyl)-4-ethyl-1,3-dioxolan-2-ylmethyl]-1H-1,2,4-triazole, 1-(4-chlorophenoxy)-1-(1H-1,2,4-triazol-1-yl)-3,3-dimethylbutan-2-one and the like.

The following examples are intended to illustrate and not to limit the scope of the present invention.

EXAMPLE I

To a solution of 6.5 parts of sodium hydroxide in 120 parts of water are added 12.5 parts of carbon disulfide, while cooling ($\pm 10°$ C.). Then there are added dropwise 23 parts of 1-phenylcyclopropylmethylamine (exothermic reaction). The whole is stirred for 30 minutes at room termperature. At a temperature of 30° C., there are added dropwise 17 parts of ethyl chloroformate (exothermic reaction: cooling is necessary). Upon completion, the mixture is stirred for 3 hours at 50° C. The product is extracted with benzene. The organic layer is dried and evaporated. The residue is distilled twice, yielding 18 parts of (1-phenylcyolopropylmethyl)isothiocyanate; bp. 150° C. at 10 mm pressure; $n_D^{20}$:1.5831; $d_{20}^{20}$:1.0917.

Following the same procedure and using equivalent amounts of the appropriate starting materials there are also prepared:

[1-(4-chlorophenyl)cyclopropylmethyl]isothiocyanate; bp. 131°–133° C. at 0.4 mm pressure; $n_D^{20}$:1.5936; $d_{20}^{20}$:1.2022;

[1-(4-methoxyphenyl)cyclopropylmethyl]isothiocyanate; bp. 120° C. at 0.1 mm pressure; $n_D^{20}$:1.5811; $d_{20}^{20}$:1.1286; and

[1-(4-fluorophenyl)cyclopropylmethyl]isothiocyanate; bp. 152°–153° C. at 10 mm pressure; $n_D^{20}$:1.5648; $d_{20}^{20}$:1.1674.

EXAMPLE II

A solution of 20 parts of sodium hydroxide and 300 parts of water is cooled to $\pm 10°$ C. and there are added successively 41.8 parts of carbon disulfide and then dropwise 95 parts of 1-phenyl-cyclopentylmethylamine (exothermic reaction). Upon completion, the cooling-bath is removed and the whole is stirred at 30 minutes at room temperature. Then there are added dropwise at 30° C., 54.25 parts of ethyl chloroformate (exothermic reaction: cooling is necessary). The whole is stirred for 3 hours at 50° C. The reaction mixture is cooled and the product is extracted with benzene. The extract is dried, filtered and evaporated. The oily residue is distilled, yielding 86 parts of (1-phenylcyclopentylmethyl)isothiocyanate; bp. 125° C. at 0.2 mm pressure; $n_D^{20}$:1.5848; $d_{20}^{20}$:1.0910.

Following the same procedure and using equivalent amounts of the appropriate starting materials there are also prepared:

[1-(4-fluorophenyl)cyclopentylmethyl]isothiocyanate; bp. 120° C. at 0.2 mm pressure;

[1-(4-chlorophenyl)cyclopentylmethyl]isothiocyanate; mp. 48° C.; and

[1-(4-methoxyphenyl)cyclopentylmethyl]isothiocyanate; mp. 69.5° C.

EXAMPLE III

A solution of 11 parts of potassium hydroxide in 200 parts of water is cooled to about 10° C. and there are added successively 22.8 parts of carbon disulfide and then dropwise 42 parts of 1-(2-thienyl)cyclopropylmethylamine (exothermic reaction). Upon completion, the whole is stirred for 30 minutes at room temperature. Then there are added at 30° C., 29.8 parts of ethyl chloroformate (exothermic reaction: cooling is necessary). The whole is stirred for 3 hours while heating at 50° C. The reaction mixture is cooled and the product is extracted with benzene. The extract is dried, filtered and evaporated. The oily residue is distilled twice, yielding 40 parts of [1-(2-thienyl)cyclopropylmethyl]isothiocyanate; bp. 140°–150° C. at 10 mm pressure; $n_D^{20}$:1.6008; $d_{20}^{20}$:1.1911.

EXAMPLE IV

A solution of 21.2 parts of sodium hydroxide in 500 parts of water is cooled to 10° C. and there is added successively 45.6 parts of carbon disulfide and then dropwise 95.83 parts of 1-(2-thienyl)-cyclopentanemethylamine (exothermic reaction). After the addition is complete, the whole is stirred for 30 minutes at room temperature. Then there are added 57.5 parts of ethyl chloroformate at 30° C. (exothermic reaction: cooling is necessary). The whole is stirred for 3 hours at 50° C. and further stirred overnight without heating. The product is extracted with benzene. The extract is dried, filtered and evaporated. The residue is poured onto 350 parts of water and the whole is heated for 3 hours at 80°–90° C. The mixture is cooled and the product is extracted with dichloromethane. The extract is dried, filtered and evaporated. The oily residue is distilled twice, yielding 88 parts of [1-(2-thienyl)cyclopentylmethyl]isothiocyanate; bp. 110° C. at 0.1 mm pressure; $n_D^{20}$:1.5960; $d_{20}^{20}$:1.1743.

EXAMPLE V

Following the procedure described in Example II and using equivalent amounts of the appropriate starting materials there are also prepared:
[1-(4-methylphenyl)cyclopentylmethyl]isothiocyanate;
[1-(2-cyano-3-ethylthiophenyl)cyclopentylmethyl]isothiocyanate;
[1-(2-amino-4-nitrophenyl)cyclopentylmethyl]isothiocyanate;
[1-(4-trifluoromethylphenyl)cyclopentylmethyl]isothiocyanate;
[1-(4-chloro-3-thienyl)cyclopentylmethyl]isothiocyanate;
[1-(2-naphthalenyl)cyclopentylmethyl]isothiocyanate;
[1-(2-pyridinyl)cyclopentylmethyl]isothiocyanate;
(1-phenylcyclobutylmethyl)isothiocyanate;
[1-(4-methylphenyl)cyclobutylmethyl]isothiocyanate;
[1-(3-ethoxyphenyl)cyclobutylmethyl]isothiocyanate;
[1-(3-methylthiophenyl)cyclobutylmethyl]isothiocyanate;
[1-(4-cyano-2,6-dibromophenyl)cyclobutylmethyl]isothiocyanate;
[1-(2-amino-4-nitrophenyl)cyclobutylmethyl]isothiocyanate;
[1-(2-thienyl)cyclobutylmethyl]isothiocyanate;
[1-(4-chloro-2-thienyl)cyclobutylmethyl]isothiocyanate;
[1-(2-naphthalenyl)cyclobutylmethyl]isothiocyanate;
[1-(3-pyridinyl)cyclobutylmethyl]isothiocyanate;
[1-(2-ethylphenyl)cyclohexylmethyl]isothiocyanate;
[1-(2-chloro-3-methylthiophenyl)cyclohexylmethyl]isothiocyanate;
[1-(3-propyloxyphenyl)cyclohexylmethyl]isothiocyanate;
[1-(2-amino-4-nitrophenyl)cyclohexylmethyl]isothiocyanate;
[1-(2-cyano-4-trifluoromethylphenyl)cyclohexylmethyl]isothiocyanate;
[1-(5-bromo-3-thienyl)cyclohexylmethyl]isothiocyanate;
[1-(1-naphthalenyl)cyclohexylmethyl]isothiocyanate.
[1-(1-pyridinyl)cyclohexylmethyl]isothiocyanate; and
(1-phenylcyclohexylmethyl)isothiocyanate.

EXAMPLE VI

Following the procedure described in Example I and using equivalent amounts of the appropriate starting materials there are also prepared:
[1-(4-propylphenyl)cyclopropylmethyl]isothiocyanate;
[1-(2-amino-5-methylphenyl)cyclopropylmethyl]isothiocyanate;
[1-(4-cyano-2-nitrophenyl)cyclopropylmethyl]isothiocyanate;
[1-(3-trifluoromethylphenyl)cyclopropylmethyl]isothiocyanate;
[1-(5-bromo-2-thienyl)cyclopropylmethyl]isothiocyanate;
[1-(1-naphthalenyl)cyclopropylmethyl]isothiocyanate; and
[1-(4-pyridinyl)cyclopropylmethyl]isothiocyanate.

What we claim is:
1. A chemical compound selected from the group consisting of an (1-arylcycloalkylmethyl)isothiocyanate having the formula

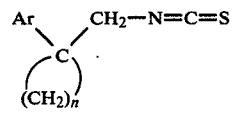

wherein
Ar is a member selected from the group consisting of thienyl, halothienyl, naphthalenyl, pyridinyl, phenyl and substituted phenyl, said substituted phenyl having from 1 to 3 substituents, each independently selected from the group consisting of lower alkyl, lower alkyloxy, lower alkylthio, halo, amino, nitro, cyano and trifluoromethyl; and
n is an integer of from 2 to 5 inclusive.
2. A chemical compound selected from the group consisting of (1-phenylcyclopropylmethyl)isothiocyanate.
3. A chemical compound selected from the group consisting of [1-(2-thienyl)cyclopropylmethyl]isothiocyanate.
4. A composition for combating fungi, bacteria and insects comprising an inert carrier material and as an active ingredient an effective amount of a compound selected from the group consisting of an (1-arylcycloalkylmethyl)isothiocyanate having the formula

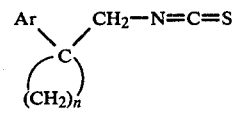

wherein
Ar is a member selected from the group consisting of thienyl, halothienyl, naphthalenyl, pyridinyl, phenyl and substituted phenyl, said substituted phenyl having from 1 to 3 substituents, each independently selected from the group consisting of lower alkyl, lower alkyloxy, lower alkylthio, halo, amino, nitro, cyano and trifluoromethyl; and
n is an integer of from 2 to 5 inclusive.

* * * * *